United States Patent [19]

Norcini et al.

[11] Patent Number: 5,506,259
[45] Date of Patent: Apr. 9, 1996

[54] β-MERCAPTO-PROPANAMIDE DERIVATIVES USEFUL IN THE TREATMENT OF CARDIOVASCULAR DISEASES

[75] Inventors: Gabriele Norcini, Vizzola Ticino; Francesco Santangelo, Milan, both of Italy

[73] Assignee: Zambon Group S.p.A., Vicenza, Italy

[21] Appl. No.: 281,105

[22] Filed: Jul. 27, 1994

[30] Foreign Application Priority Data

Jul. 30, 1993 [IT] Italy .................................. MI93A1723

[51] Int. Cl.$^6$ .................... A61K 31/40; C07D 207/34
[52] U.S. Cl. ................... 514/423; 514/426; 514/447; 514/472; 514/343; 514/336; 548/557; 548/558; 548/535; 548/532; 548/531; 549/69; 549/480; 546/281; 546/283; 546/284
[58] Field of Search ................... 549/69, 480; 548/557, 548/558, 535, 532, 531; 514/423, 426, 447, 472

[56] References Cited

U.S. PATENT DOCUMENTS 4,879,309  11/1989  Doll et al. ................... 514/513

FOREIGN PATENT DOCUMENTS

| | | |
|---|---|---|
| 0115997 | 8/1984 | European Pat. Off. . |
| 0136883 | 4/1985 | European Pat. Off. . |
| 0110484 | 9/1987 | European Pat. Off. . |
| 0280627 | of 1988 | European Pat. Off. . |
| 0318859 | 6/1989 | European Pat. Off. . |
| 0364767 | 4/1990 | European Pat. Off. . |
| 0361365 | 4/1990 | European Pat. Off. . |
| 2272435 | 5/1994 | United Kingdom . |
| 9309101 | 5/1993 | WIPO . |

OTHER PUBLICATIONS

Lewis et al. Journal of Pharmaceutical Sciences Feb. 1964, vol. 53, No. 2, pp. 115–126.

*Primary Examiner*—Jane Fan
*Attorney, Agent, or Firm*—Watson Cole Stevens Davis

[57] ABSTRACT

Compounds of formula

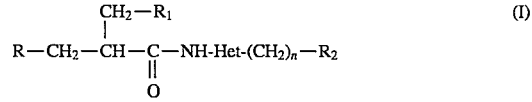

wherein R, $R_1$, $R_2$, Het and n have the meanings reported in the description, processes for their preparation and pharmaceutical compositions which contain them as active ingredients are described. The compounds of formula I are useful in the treatment of cardiovascular diseases.

4 Claims, No Drawings

β-MERCAPTO-PROPANAMIDE DERIVATIVES USEFUL IN THE TREATMENT OF CARDIOVASCULAR DISEASES

The present invention relates to β-mercapto-propanamide derivatives useful in the treatment of cardiovascular diseases and, more particularly, it relates to N-heteroaryl substituted β-mercapto-propanamide derivatives useful in the treatment of cardiovascular diseases as inhibitors of the metabolism of vasoactive peptides.

The pharmacologic interest towards the study of molecules which inhibit the metabolism of vasoactive peptides derives from the role that said peptides exert on the cardiocirculatory system. For instance, among the inhibitors of the metabolism of vasoactive peptides, the so-called NEP-inhibitors and ECE-inhibitors hold particular interest.

In particular, NEP-inhibitors are able to inhibit neutral endopeptidase enzyme (NEP), also called enkephalinase, which is responsible for the inactivation, not only of endogenous enkephaline, but also of atrial natriuretic factor (ANF), a vasodilator hormone secreted by heart.

ECE-inhibitors, instead, are able to inhibit endothelin converting enzyme (ECE), which is responsible for the transformation of big-endothelin into endothelin, a 21 amino acid peptide with vasoconstrictor activity.

Therefore, both ECE-inhibitors and NEP-inhibitors are useful in therapy in the treatment of hypertension, renal failure and congestive heart failure. The molecule which is considered the parent of ECE-inhibitors is phosphoramidon [N-[N-[[(6-deoxy-α-L-mannopyranosyl)oxy]hydroxyphosphinyl]-L-leucyl]-L-tryptophan], first isolated as microbial metabolite [Umezawa et al., Tetrahedron Letters, No. 1, pages 97–100, (1972)] and subsequently studied as inhibitor of the metabolism of vasoactive peptides [see, for instance, Matsumura et al., European Journal of Pharmacology, 185 (1990), 103–106].

The molecule which is considered the parent of NEP-inhibitors is thiorphan [DL-(3-mercapto-2-benzylpropanoyl)glycine], first described by Roques et al. in Nature, Vol. 288, pages 286–288, (1980). Several molecules with NEP-inhibitory activity, other than thiorphan, are described in the literature.

Some of them are chemically related to the structure of β-mercapto-propanamides.

The International patent application No. WO 93/09101 (Fujisawa Pharmaceutical Co. Ltd.) describes β-mercapto-propanamides of formula

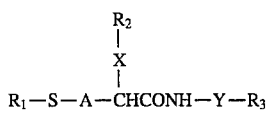

wherein $R_1$ is hydrogen or a protecting group; $R_2$ is a lower alkyl or a phenyl optionally substituted by a lower alkylenedioxy; $R_3$ is tetrazolyl, thiazolyl or thiadiazolyl optionally substituted by acyl or acyl-lower alkyl groups; A is a lower alkylene; X is a lower alkylene or S and Y is a single bond or a lower alkylene.

These compounds are NEP-inhibitors.

The European patent application No. 0361365 (E. R. Squibb & Sons, Inc.) describes β-mercapto-propanamides of formula

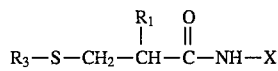

wherein $R_1$ is, among others, hydrogen, alkyl, haloalkyl, aryl or arylalkyl; X is a phenyl or a cyclohexyl, substituted in 3 or 4 by a $COOR_2$ group; $R_2$ is hydrogen, alkyl, benzyl, benzhydryl, etc.; $R_3$ is hydrogen or acyl.

These compounds are NEP-inhibitors.

The European patent application No. 0364767 (Schering Corporation) describes β-mercapto-propanamides of formula

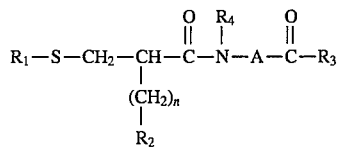

wherein $R_1$ is hydrogen or acyl; $R_2$ is aryl or heteroaryl; —$COR_3$ is a carboxylic, ester or amide residue; n is 0–3; $R_4$ is hydrogen, alkyl or arylalkyl and A is a group selected among optionally substituted phenyl, naphthyl, diphenyl, phenoxyphenyl, phenylthiophenyl, phenylmethylphenyl and pyridyl.

These compounds are able to potentiate the anti-hypertensive and natriuretic action of endogenous ANF and are useful in the treatment of congestive heart failure and of hypertension.

Other examples of the compounds known in the literature, which are structurally related to the class of β-mercapto-propanamides, do not present instead an activity on the cardiocirculatory system, but in general on the central nervous system.

The European patent N. 0110484 (SIMES Società Italiana Medicinalie Sintetici S.p.A., now Zambon Group S.p.A.) describes, among others, β-mercapto-propanamides of formula

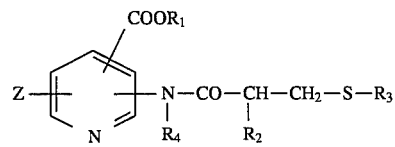

wherein Z is hydrogen, alkyl, halogen, alkoxy; $R_1$ is hydrogen, alkyl, arylalkyl, aryl; $R_2$ is hydrogen, alkyl, arylalkyl; $R_3$ is hydrogen or acyl; $R_4$ is hydrogen or alkyl. These compounds are useful as analgesics, anti-hypertensives, for the treatment of drug addiction and of psychological disturbances. The European patent application N. 0115997 (Roussel-Uclaf) describes, among others, β-mercapto-propanamides of formula

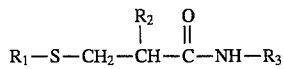

wherein $R_1$ is hydrogen or acyl; $R_2$ is, among others, hydrogen, optionally substituted alkyl, aryl or arylalkyl; $R_3$ is a heterocycle selected among thiazolyl, 4,5-dihydrothiazolyl, pyridyl, oxazolyl, isoxazolyl, imidazolyl, pirimidyl, tetrazolyl, benzimidazolyl, benzothiazolyl or benzoxazolyl optionally substituted by alkyl or $R_3$ is a phenyl optionally substituted by a radical selected among alkyl, alkoxy, hydroxy, nitro, halogen, trifluoromethyl, carboxymethyl, alkoxycarbonylmethyl, arylalkoxy, amino, monoalkylamino, dialkylamino.

These compounds are useful as analgesics.

The European patent application N. 0280627 (Roussel-Uclaf) describes α-mercaptomethyl-benzenepropanamides of formula

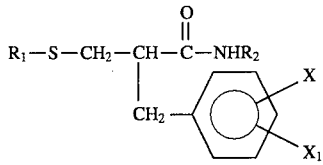

wherein $R_1$ is hydrogen or acyl; X and $X_1$ are hydrogen, alkyl, alkoxy, hydroxy, halogen or trifluoromethyl; $R_2$ is pyrrolidinyl, morpholinyl, piperidinyl, piperazinyl, tetrahydrothiazinyl or hexahydroazepinyl optionally substituted by one or more alkyl, alkoxy, hydroxy, nitro, trifluoromethyl, acyl groups and halogen.

These compounds are endowed with analgesic, psychotropic, antidepressant and anxiolythic activity.

The European patent application N. 0318859 (Dainippon Pharmaceutical Co. Ltd.) describes β-mercapto-propanamides of formula

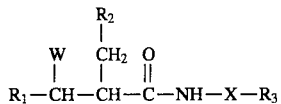

wherein $R_1$ is a SH group or a biological precursor thereof; W is hydrogen, alkyl or arylalkyl; $R_2$ is aryl, heterocycle or alkyl, optionally substituted; X is a cycloalkylene, cycloalkylidene or a phenylene, optionally substituted or fused with another ring; $R_3$ is a carboxyl or a biological precursor thereof.

These compounds are useful as analgesics.

We have now found β-mercapto-propanamides derivatives N-substituted by a 5 membered heterocycle which are endowed with a remarkable NEP-inhibitory activity and ECE-inhibitory activity.

Therefore, object of the present invention are β-mercapto-propanamides of formula

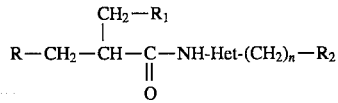

wherein

R is a mercapto group or an $R_3COS$ group convertible into the organism to the mercapto group; $R_3$ is a $C_1$–$C_4$ alkyl group;

$R_1$ is a hydrogen atom, a phenyl group or a 5 or 6 membered heterocycle containing 1 or 2 heteroatoms selected among nitrogen, oxygen and sulphur, optionally substituted by one or two groups selected among $C_1$–$C_4$ alkyl or alkoxy groups, hydroxy, halogen and trifluoromethyl groups;

$R_2$ is a carboxylic group or a $COOR_4$ or

group convertible into the organism to the carboxylic group; $R_4$ is a $C_1$–$C_4$ alkyl group or a phenylalkyl having from 1 to 4 carbon atoms in the alkyl moiety; $R_5$ and $R_6$, the same or different, are hydrogen atoms, $C_1$–$C_4$ alkyl or $C_5$–$C_7$ cycloalkyl groups;

n is 0 or 1;

Het is a 5-membered heterocycle of formula

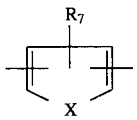

wherein X is an oxygen or sulphur atom or an NH group; $R_7$ is a hydrogen atom, a $C_1$–$C_4$ alkyl group or a phenyl optionally substituted by $C_1$–$C_4$ alkoxy groups;

and their pharmaceutically acceptable salts.

The compounds of formula I have at least an asymmetric carbon atom and may therefore exist in the form of stereoisomers.

The compounds of formula I in the form of stereoisomeric mixture as well as in the form of single stereoisomers are object of the present invention.

The compounds of formula I are endowed with both NEP-inhibitory and ECE-inhibitory activity and are useful in the treatment of cardiovascular diseases such as hypertension, renal failure and congestive heart failure.

In the present description, unless otherwise specified, with the term $C_1$–$C_4$ alkyl we intend a straight or branched $C_1$–$C_4$ alkyl such as methyl, ethyl, n.propyl, isopropyl, n.butyl, isobutyl, sec.butyl and t.butyl; with the term $C_5$–$C_7$ cycloalkyl we intend cyclopentyl, cyclohexyl and cycloheptyl; with the term $C_1$–$C_4$ alkoxy we intend a straight or branched $C_1$–$C_4$ alkoxy such as methoxy, ethoxy, n.propoxy, isopropoxy, n.butoxy, isobutoxy, sec.butoxy and t.butoxy. With the term 5- or 6-membered heterocycle containing 1 or 2 heteroatoms selected among nitrogen, oxygen and sulphur we intend a heterocycle preferably selected among thiazole, oxazole, isothiazole, isoxazole, pyrazole, imidazole, thiophene, pyrrole and pyridine. Preferred compounds are the compounds of formula I wherein R is a mercapto group or an $R_3COS$ group wherein $R_3$ is methyl; $R_2$ is a carboxylic group.

Still more preferred compounds are the compounds of formula I wherein R is a mercapto group or an $R_3COS$ group wherein $R_3$ is methyl; $R_2$ is a carboxylic group; $R_1$ is phenyl or pyridyl, optionally substituted by a $C_1$–$C_4$ alkyl or alkoxy group or by a halogen atom and Het is a heterocycle of formula

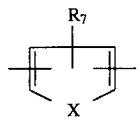

wherein X is an oxygen or sulphur atom or an NH group and $R_7$ is a hydrogen atom.

It is evident that the compounds of formula I, wherein R is an $R_3COS$ group convertible into the organism to the mercapto group or $R_2$ is a $COOR_4$ or

group, convertible into the organism to the carboxylic group, are biological precursors (pro-drugs) of the corresponding compounds of formula I wherein R is a mercapto group (R=SH) and $R_2$ is a carboxylic group ($R_2$=COOH).

The preparation of the compounds of formula I, object of the present invention, is carried out by reacting a derivative of the β-mercapto-propionic acid of formula

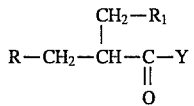  (II)

wherein R and $R_1$ have the above reported meanings and Y is a halogen atom, preferably chlorine or bromine; and a compound of formula $$H_2N\text{—Het—}(CH_2)_n\text{—}R_2 \quad (III)$$

wherein $R_2$, Het and n have the above reported meanings; in a suitable solvent, in the presence of a base; followed by optional hydrolysis.

Preferably the intermediates of formula II and III are used in a protected form (R=$R_3$COS and $R_2$=COOR$_4$ or

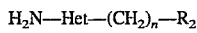

affording thus the corresponding compounds of formula I wherein R=$R_3$COS and $R_2$=COOR$_4$ or $R_5$ CON—$R_6$ from which, by hydrolysis, the compounds of formula I wherein R=SH and $R_2$=COOH are obtained.

The compounds of formula II are known or easily prepared according to conventional methods (see for instance the British patent n. 1576161 in the name of Squibb E.R. & Sons Inc.) from the corresponding acids of formula

  (IV)

wherein R and $R_1$ have the above reported meanings. Also the intermediates of formula III are known or easily prepared with known methods.

For a bibliographic reference to the preparation of the compounds of formula III see for instance Michel Sy et al., Bull. Soc. Chim. Fr., 1276–1277, (1963) and Moses Lee et al., J. Org. Chem., 53, No. 9, 1855–1859, (1988).

The compounds of formula I in the form of single stereoisomers are prepared by stereoselective synthesis or by separation of the stereoisomeric mixture according to conventional techniques.

The compounds of formula I are active as NEP-inhibitors and ECE-inhibitors and are useful in the treatment of cardiovascular diseases such as hypertension, renal failure and congestive heart failure. The NEP-inhibitory activity of the compounds of formula I was evaluated by means of in vitro tests as percentage of inhibition in the formation of [$^3$H]-Tyr-Gly-Gly, a metabolite of [$^3$H][Leu$^5$]-enkephaline (see example 26).

The inhibitory activity, expressed as IC$_{50}$ (nM), of the compounds of formula I resulted to be substantially comparable with that of the reference compounds.

Thiorphan, the compound N-(3-carboxyphenyl)-3-mercapto-2-benzyl-propanamide, described in the aforementioned European patent application No. 0361365 (E.R. Squibb & Sons, Inc.) and the compound N-4-carboxymethyl-2-thiazolyl)-3-mercapto-2-benzyl-propanamide, described in the aforementioned International patent application No. WO 93/09101 (Fujisawa Pharmaceutical Co. Ltd.) were used as reference compounds (see table 1).

The ECE-inhibitory activity of the compounds of formula I was evaluated by means of in vitro tests for the inhibition of endothelin formation and resulted to be significantly greater than that of phosphoramidon (see example 26).

For the practical use in therapy the compounds of formula I can be formulated in solid or liquid pharmaceutical compositions, suitable for oral or parenteral administration.

Therefore the pharmaceutical compositions containing one or more compounds of formula I, as active ingredient, in admixture with a carrier for pharmaceutical use are a further object of the present invention.

Specific examples of the pharmaceutical compositions according to the present invention are tablets, coated tablets, capsules, granulates, solutions and suspensions suitable for oral administration, solutions and suspensions suitable for parenteral administration. The pharmaceutical compositions object of the present invention may contain one or more compounds of formula I in association with other active ingredients such as for instance ACE-inhibitors. The pharmaceutical compositions object of the present invention are prepared according to conventional techniques.

The daily dose of compound of formula I will depend on different factors such as the seriousness of the disease, the individual response of the patient, the use of biological precursors and the kind of formulation but it is usually comprised between 0.1 mg and 50 mg per Kg of body weight in a single dose or divided into more daily doses.

With the aim of better illustrating the present invention the following examples are now given.

EXAMPLE 1

Preparation of N-(2-ethoxycarbonyl-4-thienyl)-3-acetylthio-2-benzyl-propanamide (compound 1)

3-Acetylthio-2-benzyl-propionic acid (2.9 g; 12 mmoles) and dimethylformamide (3 drops) were dissolved in thionyl chloride (3 ml). After 16 hours at room temperature the solvent was evaporated under vacuum and the residue was collected twice with toluene (10 ml), evaporating to dryness each time.

The obtained oil was dissolved in toluene (30 ml) and the solution was cooled with ice. Then a solution of 4-amino-2-ethoxycarbonyl-thiophene (1.8 g; 10.5 mmoles) and triethylamine (1.69 ml) in toluene (37 ml) was added dropwise.

After 5 hours under stirring at room temperature, the reaction mixture was diluted with water (30 ml) and extracted with ethyl acetate.

The organic phase was dried on sodium sulphate and the solvent was evaporated under vacuum.

The oil was purified by chromatography (silica gel, eluent n.hexane: ethyl acetate=7:3) affording N-(2-ethoxycarbonyl-4-thienyl)-3-acetylthio-2-benzyl-propanamide (1.4 g; 32.2% yield).

$^1$H-NMR (200 MHz, CDCl$_3$): δ (ppm): 1.35 (t, 3H); 2.32 (s, 3H); 2.68 (m, 1H); 2.85–3.30 (m, 4H); 4.32 (q, 2H); 7.20 (m, 5H); 7.46 (d, 1H); 7.69 (d, 1H).

EXAMPLE 2

Preparation of N-(2-carboxy-4-thienyl)-3-mercapto-2-benzyl-propanamide (compound 2)

A solution of N-(2-ethoxycarbonyl-4-thienyl)-3-acetylthio-2-benzyl-propanamide (1.35 g; 34 mmoles), prepared as described in example 1, and sodium hydroxide (0.407 g; 10.2 mmoles) in water (5.76 ml) and methanol (14 ml) was kept under stirring for 16 hours at 20° C. under nitrogen.

Methanol was evaporated under vacuum and the mixture was acidified with diluted hydrochloric acid to pH about 4.

After extraction with ethyl acetate, the organic phase was washed with water and dried on sodium sulphate.

By evaporating the solvent under vacuum an oil was obtained which crystallizes from methylene chloride:hexane=1:9, affording N-(2-carboxy-4-thienyl)-3-mercapto-2-benzyl-propanamide (0.43 g; 39.4% yield).

m.p. 174°–177° C.

$^1$H-NMR (200 MHz, DMSO-$d_6$): δ (ppm): 2.32 (t, 1H); 2.53–2.92 (m, 5H); 7.11–7.30 (m, 5H); 7.62 (d, 1H); 7.70 (d, 1H).

EXAMPLE 3

Preparation of N-(2-ethoxycarbonyl-4-pyrrolyl)-3-acetylthio-2-benzyl-propanamide (compound 3)

By working in a way similar to that described in example 1 but substituting 4-amino-2-ethoxycarbonyl-thiophene with 4-amino-2-ethoxycarbonyl-pyrrole, N-(2-ethoxycarbonyl-4-pyrrolyl)-3-acetylthio-2-benzyl-propanamide was obtained (55.6% yield).

$^1$H-NMR (200 MHz, CDCl$_3$): δ (ppm): 1.30 (t, 3H); 2.32 (s, 3H); 2.66 (m, 1H); 2.80–3.30 (m, 4H); 4.27 (q, 2H); 6.52 (dd, 1H); 7.22 (m, 5H); 7.37 (dd, 1H).

EXAMPLE 4

Preparation of N-(2-carboxy-4-pyrrolyl)-3-mercapto-2-benzyl-propanamide (compound 4)

By working in a way similar to that described in example 2, after chromatography on silica gel (eluent CH$_2$Cl$_2$:CH$_3$OH:CH$_3$COOH=90:10:1) and crystallization from CH$_2$Cl$_2$:hexane=1:2, N-(2-carboxy-4-pyrrolyl)-3-mercapto-2-benzyl-propanamide (4.93 g; 46.3% yield) white crystalline solid was obtained.

m.p. 169°–172° C.

$^1$H-NMR (200 MHz, DMSO-$d_6$): δ (ppm): 2.22 (t, 1H); 2.55–2.94 (m, 5H); 6.56 (dd, 1H); 7.11–7.30 (m, 6H); 9.84 (bs, 1H); 11.41 (bs, 1H).

EXAMPLE 5

Preparation of ethyl 2-ethoxycarbonyl-3-(3-pyridyl)-propionate

Diethyl malonate (10.176 ml; 67.1 mmoles) was added dropwise to a solution obtained by dissolving metallic sodium (1.543 g; 67.1 mmoles) in anhydrous ethanol (20 ml) heated at 50° C. The solution was kept under stirring at 50° C. for 30 minutes and then cooled at room temperature.

3-Chloromethyl-pyridine (5 g; 39.2 mmoles) was added dropwise and the reaction mixture was heated under reflux for 90 minutes. After evaporating the mixture under vacuum, the residue was collected with ethyl acetate and evaporated to dryness.

The obtained crude was purified by silica gel chromatography (eluent hexane:ethyl acetate=1:1) affording ethyl 2-ethoxycarbonyl-3-(3-pyridyl)-propionate (4.83 g; 49% yield).

$^1$H-NMR (200 MHz, CDCl$_3$): δ (ppm): 1.18 (t, 6H); 3.19 (d, 2H); 3.60 (t, 1H); 4.13 (q, 4H); 7.12–7.21 (m, 1H); 7.51 (dt, 1H); 8.41–8.47 (m, 2H).

EXAMPLE 6

Preparation of 2-carboxy-3-(3-pyridyl)-propionic acid

A solution of potassium hydroxide at 85% (96.8 g; 1.47 moles) in water (300 ml) was added to a solution of ethyl 2-ethoxycarbonyl-3-(3-pyridyl)-propionate (168 g; 0.668 moles), prepared as described in example 5, in dioxane (1680 ml).

The reaction mixture was kept under stirring at room temperature for 4 hours.

The reaction mixture was then neutralized by adding hydrochloric acid 12N (122.5 ml) and evaporated to dryness under vacuum.

The residue was collected with ethanol (4×750 ml) and the mixture was kept at boiling temperature before filtering off the precipitate.

The solution was evaporated to dryness under vacuum and a crude product (128 g) was obtained which, crystallized from ethanol (1000 ml, afforded 2-carboxy-3-(3-pyridyl)-propionic acid (93.5 g; 72% yield).

m.p. 128°–129° C.

$^1$H-NMR (200 MHz, DMSO-$d_6$): δ (ppm): 3.40 (d, 2H); 3.64 (t, 1H); 7.26–7.33 (m, 1H); 7.67 (dt, 1H); 8.37–8.43 (m, 2H).

EXAMPLE 7

Preparation of 2-(3-pyridylmethyl)-propenoic acid

An aqueous solution 7.9N of dimethylamine (2.28 ml; 0.018 moles) was added at 10° C. to 2-carboxy-3-(3-pyridyl)-propionic acid (3.5 g; 0.018 moles), prepared as described in example 6.

The reaction mixture was cooled at 0° C. and formaldehyde (1.48 g; 0.018 moles) was added dropwise.

At the end, the reaction mixture was kept under stirring at room temperature overnight.

By evaporating to dryness under vacuum and by heating the obtained residue at 125° C. under vacuum for 4 hours, a crude was obtained which, chromatographed on silica gel (eluent CH$_2$Cl$_2$:CH$_3$OH:CH$_3$COOH=90:10:1), afforded 2-(3-pyridylmethyl)-propenoic acid (1.8 g; 61.3% yield).

m.p. 101°–102° C.

$^1$H-NMR (200 MHz, DMSO-$d_6$): δ (ppm): 3.58 (s, 2H); 5.62 (s, 1H); 6.15 (s, 1H); 7.25–7.38 (m, 1H); 7.60 (dt, 1H); 8.42 (m, 2H).

EXAMPLE 8

Preparation of 3-acetylthio-2-(3-pyridylmethyl)-propionic acid

A mixture of 2-(3-pyridylmethyl)-propenoic acid (10 g; 0.061 moles), prepared as described in example 7, and thioacetic acid (4.56 ml; 0.064 moles) was heated at 100° C. for 1 hour.

The reaction mixture was then evaporated to dryness under vacuum and the residue was purified by silica gel chromatography (eluent CH$_2$Cl$_2$:CH$_3$OH:CH$_3$COOH= 95:5:0.5) obtaining oily 3-acetylthio-2-(3-pyridylmethyl)-propionic acid (10.5 g; 72% yield).

$^1$H-NMR (200 MHz, CDCl$_3$): δ (ppm): 2.17 (s, 3H); 2.37–2.57 (m, 5H); 6.66 (dd, 1H); 6.83 (dt, 1H); 8.19 (d, 2H).

EXAMPLE 9

Preparation of N-(2-ethoxycarbonyl-4-thienyl)-3-acetylthio-2-(3-pyridylmethyl)-propanamide (compound 5)

A solution of 3-acetylthio-2-(3-pyridylmethyl)-propionic acid (1 g; 4.2 mmoles), prepared as described in example 8, in thionyl chloride (5 ml) and in the presence of dimethylformamide (1 drop) was left at room temperature for 12 hours.

Said mixture was diluted with pyridine (10 ml) and added dropwise to a solution of 4-amino-2-ethoxycarbonyl-thiophene (0.65 g; 3.78 mmoles) in pyridine (5 ml).

After 3 hours at room temperature the reaction mixture was evaporated to dryness under vacuum and the residue was collected with water (20 ml) and extracted with ethyl acetate (3×20 ml).

The collected organic phases were dried on sodium sulphate and evaporated to dryness under vacuum.

The obtained crude was chromatographed on silica gel (eluent $CH_2Cl_2:CH_3OH=95:5$) obtaining an oil which, collected with ethyl ether and filtered, afforded N-(2-ethoxycarbonyl-4-thienyl)-3-acetylthio-2-(3-pyridylmethyl)-propanamide (0.57 g; 38.5% yield).

$^1$H-NMR (200 MHz, $CDCl_3$): δ (ppm): 1.33 (t, 3H); 2.33 (s, 3H); 2.72–3.27 (m, 5H); 4.30 (q, 2H); 7.18 (dd, 1H); 7.52 (m, 2H); 7.79 (d, 1H); 8.13 (d, 1H); 8.38 (dd, 1H); 9.58 (s, 1H).

EXAMPLE 10

Preparation of N-(2-carboxy-4-thienyl)-3-mercapto-2-(3-pyridylmethyl)-propanamide (compound 6)

A solution of sodium hydroxide 10.8N (0.437 ml; 0.0047 moles) in water (5 ml) was added to a solution of N-(2-ethoxycarbonyl-4-thienyl)-3-acetylthio-2-(3-pyridylmethyl)-propanamide (0.57 g; 1.45 mmoles), prepared as described in example 9, in methanol (10 ml).

The reaction mixture was kept under stirring at room temperature for 12 hours.

At the end, it was evaporated to dryness under vacuum and the residue was collected with water (10 ml) and washed with ethyl acetate. The aqueous phase was acidified to pH 4 with hydrochloric acid 1N and subsequently extracted with ethyl acetate.

The organic phase was dried on sodium sulphate and evaporated to dryness under vacuum; the obtained crude was collected with ethyl ether and filtered affording N-(2-carboxy-4-thienyl)-3-mercapto-2-(3-pyridylmethyl)-propanamide (0.1 g; 21.4% yield).

m.p. 115°–118° C.

Mass (Chemical ionization, isobutane): ($M^+$+H): 323

$^1$H-NMR (200 MHz, DMSO-$d_6$): δ (ppm): 2.57–2.91 (m, 5H); 7.27 (dd, 1H); 7.52–7.63 (dt, 1H); 7.72 (d, 1H); 8.37 (dd, 2H); 10.39 (s, 1H).

EXAMPLE 11

Preparation of ethyl 3-(4-chlorophenyl)-2-diethoxyphosphinyl-propionate

Sodium hydride (3.12 g; 0.130 moles) was added dropwise to a solution of ethyl diethoxyphosphinylacetate (37 ml; 0.186 moles) in anhydrous dimethylformamide (150 ml), kept at 0° C. under nitrogen atmosphere.

After 3 hours at a temperature of 0°–5° C., a solution of 4-chlorobenzyl chloride (20 g; 0.124 moles) in dimethylformamide (90 ml) was added at 0° C.

At the end, the reaction mixture was kept under stirring at room temperature for 48 hours, diluted with water (400 ml) containing concentrate hydrochloric acid (5 ml) and extracted with ethyl acetate (3×50 ml).

The collected organic phases were washed twice with water (50 ml), dried on sodium sulphate and evaporated to dryness under vacuum. The residue was distilled in Vigreaux column (0.7 mm Hg; 165° C.) obtaining oily ethyl 3-(4-chlorophenyl)-2-diethoxyphosphinyl-propionate (19 g; 44% yield).

$^1$H-NMR (200 MHz, $CDCl_3$): δ (ppm): 1.13 (t, 3H); 1.33 (t, 6H); 3.05–3.24 (m, 3H); 4.01–4.22 (m, 6H); 7.07–7.23 (m, 4H).

EXAMPLE 12

Preparation of ethyl 2-(4-chlorobenzyl)-acrylate

Potassium carbonate (10 g; 0.072 moles) was added to a solution of ethyl 3-(4-chlorophenyl)-2-diethoxyphosphinyl-propionate (22 g; 0.065 moles), prepared as described in example 11, in formaldehyde (40 ml).

The reaction mixture was heated under reflux for 4 hours.

At the end, it was diluted with water (100 ml), extracted with ethyl acetate (3×50 ml), dried on sodium sulphate and evaporated to dryness under vacuum.

The obtained crude which was purified by distillation (8 mm Hg; 150° C.) afforded ethyl 2-(4-chlorobenzyl)-acrylate (8.45 g; 58% yield) as oil.

$^1$H-NMR (200 MHz, $CDCl_3$): δ (ppm): 1.23 (t, 3H); 3.58 (s, 2H); 4.15 (q, 2H); 5.44 (d, 1H); 6.21 (s, 1H); 7.07–7.26 (m, 4H).

EXAMPLE 13

Preparation of 2-(4-chlorobenzyl)-propenoic acid

A solution of sodium hydroxide 12N (3.8 ml; 0.0456 moles) was added to a solution of ethyl 2-(4-chlorobenzyl)-acrylate (8.45 g; 0.038 moles), prepared as described in example 12, in methanol (40 ml).

The reaction mixture was kept under stirring at room temperature for 24 hours.

Methanol was evaporated under vacuum and the formed precipitate was collected with water (50 ml); the mixture was acidified to pH 2 with concentrate hydrochloric acid.

By extracting with ethyl acetate (3×30 ml), drying the collected organic phases on sodium sulphate and evaporating to dryness under vacuum, 2-(4-chlorobenzyl)-propenoic acid (6.6 g; 88% yield) was obtained.

m.p. 78°–86° C.

$^1$H-NMR (200 MHz, DMSO-$d_6$): δ(ppm): 2.78 (s, 2H); 4.79 (d, 1H); 6.06 (s, 1H); 6.59–6.68 (m, 4H).

EXAMPLE 14

Preparation of 3-acetylthio-2-(4-chlorobenzyl)-propionic acid

By working in a way similar to that described in example 8 and by using 2-(4-chlorobenzyl)-propenoic acid (6.7 g; 0.034 moles), prepared as described in example 13, and thioacetic acid (3.64 ml; 0.051 moles), a crude was obtained which chromatographed on silica gel (eluent ligroin:ethyl acetate=1:1) afforded 3-acetylthio-2-(4-chlorobenzyl)-propionic acid (4.36 g; 47% yield) as oil.

$^1$H-NMR (200 MHz, $CDCl_3$): δ(ppm): 2.32 (s, 3H); 2.71–3.10 (m, 5H); 7.08–7.28 (m, 4H).

EXAMPLE 15

Preparation of N-(2-ethoxycarbonyl-4-pyrrolyl)-3-acetylthio-2-(4-chlorobenzyl)-propanamide (compound 7)

A solution of 3-acetylthio-2-(4-chlorobenzyl)-propionic acid (4.36 g; 0.016 moles), prepared as described in example 14, in thionyl chloride (5 ml), in the presence of dimethylformamide (2drops), was kept at room temperature and under nitrogen atmosphere for 24 hours. After that, the excess of thionyl chloride was removed by azeotropic distillation with toluene.

Said reaction mixture was added dropwise at 0° C. and under nitrogen atmosphere to a solution of 4-amino-2-ethoxycarbonyl-pyrrole (2.46 g; 0.016 moles) and triethylamine (1.7 g; 0.017 moles) in toluene (40 ml).

After 3 hours at room temperature the reaction mixture was evaporated under vacuum and the residue was collected with ethyl ether and filtered.

The solid was crystallized from ethyl acetate:ligroin=1:2 and N-(2-ethoxycarbonyl-4-pyrrolyl)-3-acetylthio-2-(4-chlorobenzyl)-propanamide (3.5 g; 53.5% yield) was obtained.

m.p. 141°–144° C.

$^1$H-NMR (200 MHz, DMSO-$d_6$): δ(ppm): 1.25 (t, 3H); 2.29 (s, 3H); 2.69–3.01 (m, 5H); 4.20 (q, 2H); 6.61 (m, 1H); 7.11–7.35 (m, 5H); 9.89 (s, 1H); 11.60 (s, 1H).

EXAMPLE 16

Preparation of N-(2-ethoxycarbonyl-4-pyrrolyl)-2-(4-chlorobenzyl)-3-mercapto-propanamide (compound 8)

A solution of triethylamine (0.68 ml; 4.89 mmoles) in methanol (10 ml) was added to a solution of N-(2-ethoxycarbonyl-4-pyrrolyl)-3-acetylthio-2-(4-chlorobenzyl)-propanamide (1 g; 2.45 mmoles), prepared as described in example 15, in methanol (20 ml).

The reaction mixture was kept under stirring at room temperature for 3 hours, then it was acidified to pH 3 with acetic acid and diluted with water (20 ml).

After extraction with ethyl acetate (3×30 ml), the collected organic phases were dried on sodium sulphate and evaporated to dryness under vacuum.

The obtained crude was chromatographed on silica gel (eluent $CH_2Cl_2:CH_3OH$=95:5), further collected with $CH_2Cl_2$:ligroin=1:1 and filtered affording N-(2-ethoxycarbonyl-4-pyrrolyl)-2-(4-chlorobenzyl)-3-mercapto-propanamide (0.63 g; 70% yield).

m.p. 140°–143° C.

Mass (Chemical ionization, isobutane): ($M^++H$): 367

$^1$H-NMR (200 MHz, $CDCl_3$): δ(ppm): 1.30 (t, 3H); 2.49–3.03 (m, 5H); 4.28 (q, 2H); 6.59 (t, 1H); 7.03–7.24 (m, 5H); 7.36 (t, 1H); 9.09 (bs, 1H).

EXAMPLE 17

Preparation of N-(2-carboxy-4-pyrrolyl)-2-(4-chlorobenzyl)-3-mercapto-propanamide (compound 9)

By working in a way similar to that described in example 10 and by using N-(2-ethoxycarbonyl-4-pyrrolyl)-3-acetylthio-2-(4-chlorobenzyl)-propanamide (1 g; 2.45 mmoles), prepared as described in example 15, a crude was obtained which, chromatographed on silica gel (eluent $CH_2Cl_2:CH_3OH:CH_3COOH$=90:10:1) and further collected with toluene: ligroin=1:1 and filtered, afforded N-(2-carboxy-4-pyrrolyl)-2-(4-chlorobenzyl)-3-mercapto-propanamide (0.5 g; 60.2% yield).

Mass (Chemical ionization, isobutane): ($M^++H$): 339

$^1$H-NMR (200 MHz, DMSO-$d_6$): δ(ppm): 2.44–2.86 (m,5H); 6.56 (s,1H); 7.11–7.32 (m, 5H); 9.73 (s, 1H); 11.38 (bs, 1H).

EXAMPLE 18

Preparation of N-(2-ethoxycarbonyl-4-pyrrolyl)-3-acetylthio-2-(3-pyridylmethyl)-propanamide (compound 10)

N-hydroxysuccinimide (0.962 g; 8.36 mmoles) and dicyclohexylcarbodiimide (1.72 g; 8.36 mmoles) were added to a solution of 3-acetylthio-2-(3-pyridylmethyl)-propionic acid (2 g; 8.36 mmoles), prepared as described in example 8, in dioxane (50 ml).

The reaction mixture was kept under stirring at room temperature for 2 hours.

At the end, the formed precipitate was filtered off and the solution was evaporated to dryness under vacuum.

The residue was collected with chloroform (20 ml) and the solution was filtered and evaporated to dryness; this procedure was repeated twice.

The residue, collected again with dioxane (20 ml), was added to a solution of 4-amino-2-ethoxycarbonyl-pyrrole (1.29 g; 8.36 mmoles) in dioxane (20 ml).

The reaction mixture was kept under stirring at room temperature for 16 hours.

After said time, it was diluted with water (40 ml) and extracted with ethyl acetate (3×30 ml).

The collected organic phases were washed twice with water (30 ml), dried on sodium sulphate and evaporated to dryness under vacuum affording a crude which was chromatographed on silica gel (eluent $CH_2Cl_2:CH_3OH$=95:5).

N-(2-ethoxycarbonyl-4-pyrrolyl)-3-acetylthio-2-(3-pyridylmethyl)-propanamide (0.6 g; 19.3% yield) was thus obtained.

Mass (Chemical ionization, isobutane): ($M^++H$): 376

$^1$H-NMR (200 MHz, $CDCl_3$): δ(ppm): 1.23 (t, 3H); 2.30 (s, 3H); 2.74–3.18 (m, 5H); 4.20 (q, 2H); 6.55 (t, 1H); 7.10–7.18 (dd, 1H); 7.39 (t, 1H); 7.49 (dt, 1H); 8.12 (d, 1H); 8.29 (dd, 1H); 9.49 (s, 1H); 9.71 (bs, 1H).

EXAMPLE 19

Preparation of N-(2-carboxy-4-pyrrolyl)-3-mercapto-2-(3-pyridylmethyl)-propanamide (compound 11)

A solution of sodium hydroxide (0.131 g; 3.28 mmoles) in water (10 ml) was added to a solution of N-(2-ethoxycarbonyl-4-pyrrolyl)-3-acetylthio-2-(3-pyridylmethyl)-propanamide (0.56 g; 1.49 mmoles), prepared as described in example 18, in methanol (10 ml).

The reaction mixture was kept under reflux for 6 hours and sodium hydroxide (0.065 g; 1.64 mmoles) was therein added again.

After 12 hours at room temperature, methanol was evaporated and the residue was diluted with water (20 ml) while pH was brought to 7 by adding sodium bicarbonate.

The mixture was evaporated to dryness and by chromatography on silica gel (eluent $CH_2Cl_2:CH_3OH:NH_3$=79:15:1) a crude was obtained which, collected with chloroform:ethyl ether, afforded N-(2-carboxy-4-pyrrolyl)-3-mercapto-2-(3-pyridylmethyl)-propanamide (80 mg; 17.6% yield).

m.p. 85°–90° C.

$^1$H-NMR (200 MHz, DMSO-$d_6$); δ(ppm): 2.55–2.89 (m, 5H); 6.49 (m, 1H); 7.09 (m, 1H); 7.20–7.30 (dd, 1H); 7.51–7.60 (dd, 1H); 8.36 (d, 2H); 9.82 (s, 1H); 11.23 (bs, 1H).

EXAMPLE 20

Preparation of ethyl 2-diethoxyphosphinyl-3-(3-methoxyphenyl)-propionate

By working in a way similar to that described in example 11 and by using ethyl diethoxyphosphinylacetate (59 g; 0.26 moles), sodium hydride at 60% (9.33 g; 0.233 moles) and 3-methoxybenzyl chloride (20.62 g; 0.13 moles), ethyl 2-diethoxyphosphinyl-3-(3-methoxyphenyl)-propionate (34 g; 76% yield) was obtained.

$^1$H-NMR (200 MHz, $CDCl_3$): δ(ppm): 1.12 (t, 3H); 1.32 (t, 6H); 3.10–3.32 (m, 3H); 3.75 (s, 3H); 4.08–4.22 (m, 6H); 6.69–6.78 (m, 3H); 7.10–7.22 (m, 1H).

EXAMPLE 21

Preparation of ethyl 2-(3-methoxybenzyl)-acrylate

By working in a way similar to that described in example 12 and by using ethyl 2-diethoxyphosphinyl-3-(3-methoxyphenyl)-propionate (34 g; 0.0987 moles), prepared as described in example 20, ethyl 2-(3-methoxybenzyl)-acrylate (21.5 g; 98.9% yield) was obtained.

$^1$H-NMR (200 MHz, CDCl$_3$): δ(ppm); 1.25 (t, 3H); 3.69 (s, 2H); 3.77 (s, 3H); 4.17 (q, 2H); 5.45 (d, 1H); 6.21 (s, 1H); 6.70–6.80 (m, 3H); 7.14–7.23 (m, 1H).

EXAMPLE 22

Preparation of 2-(3-methoxybenzyl)-propenoic acid

By working in a way similar to that described in example 13 and by using ethyl 2-(3-methoxybenzyl)-acrylate (10 g; 0.0454 moles), prepared as described in example 21, 2-(3-methoxybenzyl)-propenoic acid (7 g; 80.2% yield) was obtained.

$^1$H-NMR (200 MHz, CDCl$_3$): δ(ppm): 3.59 (s, 2H); 3.78 (s, 3H); 5.58 (d, 1H) 6.37 (s, 1H); 6.72–6.81 (t, 3H); 7.16–7.25 (m, 1H).

EXAMPLE 23

Preparation of 3-acetylthio-2-(3-methoxybenzyl)-propionic acid

By working in a way similar to that described in example 14 and by using 2-(3-methoxybenzyl)-propenoic acid (6.2 g; 0.0323 moles), prepared as described in example 22, a crude was obtained which, chromatographed on silica gel (eluent hexane:ethyl acetate=1:1), afforded 3-acetylthio-2-(3-methoxybenzyl)-propionic acid (3.5 g; 40.4% yield).

$^1$H-NMR (200 MHz, CDCl$_3$): δ(ppm): 2.32 (s, 3H); 2.77–3.13 (m, 5H); 3.78 (s, 3H); 6.65–6.78 (m, 3H); 7.12–7.22 (m, 1H).

EXAMPLE 24

Preparation of N-(2-ethoxycarbonyl-4-pyrrolyl)-3-acetylthio-2-(3-methoxybenzyl)-propanamide (compound 12)

By working in a way similar to that described in example 15 and by using 3-acetylthio-2-(3-methoxybenzyl)-propionic acid (3.9 g; 0.0145 moles), prepared as described in example 23, thionyl chloride (1.3 ml) and a solution of 4-amino-2-ethoxycarbonyl-pyrrole (2.24 g; 0.0145 moles) in pyridine (200 ml), a crude was obtained which, chromatographed on silica gel (eluent ligroin:ethyl acetate=7:3) and further crystallized from ligroin:ethyl acetate=1:1, afforded N-(2-ethoxycarbonyl-4-pyrrolyl)-3-acetylthio-2-(3-methoxybenzyl)-propanamide (2 g; 34% yield).

$^1$H-NMR (200 MHz, CDCl$_3$): δ (ppm): 1.30 (t, 3H); 2.30 (s, 3H); 2.62–3.18 (m, 5H); 3.70 (s, 3H); 4.27 (q, 2H); 6.52 (dd, 1H); 6.65–6.77 (m, 3H); 7.06–7.23 (m, 2H); 7.37 (dd, 1H); 8.95 (bs, 1H).

EXAMPLE 25

Preparation of N-(2-carboxy-4-pyrrolyl)-3-mercapto-2-(3-methoxybenzyl)-propanamide (compound 13)

By working in a way similar to that described in example 17 and by using N-(2-ethoxycarbonyl-4-pyrrolyl)-3-acetylthio-2-(3-methoxybenzyl)-propanamide (0.98 g; 2.42 mmoles), prepared as described in example 24, a crude was obtained which, chromatographed on silica gel (eluent CH$_2$Cl$_2$:CH$_3$OH:CH$_3$COOH=90:10:1) and collected with ligroin:ethyl acetate=1:1 afforded N-(2-carboxy-4-pyrrolyl)-3-mercapto-2-(3-methoxybenzyl)-propanamide (0.520 g; 64.2% yield) as white solid.

m.p. 153°–158° C.

Mass (Chemical ionization, isobutane): (M$^+$+H): 335

$^1$H-NMR (200 MHz, DMSO-d$_6$): δ (ppm): 2.46–2.89 (m, 5H); 3.65 (s, 3H); 6.53 (m, 1H); 6.72 (m, 3H); 7.10–7.20 (m, 2H); 9.83 (s, 1H); 11.32 (bs, 1H).

EXAMPLE 26

Pharmacological activity a) In vitro NEP-inhibitory activity

The NEP-inhibitory activity in vitro was evaluated according to the method reported in the literature by C. Llorens et al., Eur. J. Pharmacol., 69, (1981), 113–116.

Membranes from kidney cortex were prepared according to the following procedure.

By working at 0°–4° C. the kidneys were removed from killed male Sprague-Dawley rats weighing approximately 300 g.

Cortex was carefully dissected, finely minced and suspended in homogenization buffer (10 mM sodium phosphate pH 7.4 containing 1 mM MgCl$_2$, 30 mM NaCl, 0.02% NaN$_3$) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use. The NEP-inhibitory activity was evaluated by using the following method.

Aliquots of the membrane suspension prepared as above described (concentration 5 μg/ml of proteins) were preincubated in the presence of an aminopeptidase inhibitor (Bestatin - 1 mM) for 10 minutes at 30° C.

[$^3$H][Leu$^5$]-enkephaline (15 nM) and buffer TRIS/HCl pH 7.4 (50 mM) were added in order to obtain a final volume of 100 μl.

Incubation (20 minutes at 30° C.) was stopped by adding 0.1M HCl (100 μl).

The formation of the metabolite [$^3$H]Tyr-Gly-Gly was quantified by chromatography on polystyrene columns (Porapak Q).

The percentage of inhibition of the metabolite formation in the membrane preparations treated with the compounds of formula I and the reference compounds in comparison to the untreated membrane preparations was expressed as IC$_{50}$ value (nM).

The used reference compounds were:

N-(3-mercapto-2-benzyl-1-oxo-propyl)glycine (thiorphan)

N-(3-carboxyphenyl)-3-mercapto-2-benzyl-propanamide (compound R-1)

N-(4-carboxymethyl-2-thiazolyl)-3-mercapto-2-benzyl-propanamide (compound R-2).

b) In vitro ECE-inhibitory activity

The ECE-inhibitory activity in vitro was evaluated according to the method reported in the literature by M. Auget et al., Eur. J. Pharmacol., 224, (1992), 101–102.

Male New Zealand rabbits (2.5–3 Kg) were sacrificed with an excess of pentobarbital and blood was drawn.

The left saphenous artery was removed and cleaned of the surrounding tissue, cut into 2–3 mm length rings and suspended in 25 ml baths containing Krebs-Henseleit solution at 37° C. and oxygenated with $O_2$ containing 5% $CO_2$. This solution was composed of (mM); NaCl, 118; KCl, 4.7; $CaCl_2$, 2.5; $KH_2PO_4$, 1.2; $MgSO_4$, 1.2; $NaHCO_3$, 2.5; glucose, 11. The preparations were kept under tension and readjusted to 1 g during the equilibration period (1 hour).

After said period, the preparations were exposed to a submaximal concentration of norepinephrine 1 μM which was repeated every 30 minutes until the response was stable. A concentration of acetylcholine 10 μM on the contraction of norepinephrine verified the presence of the endothelium.

After 30 minutes from the last contraction due to norepinephrine, a concentration of human Big endothelin $3 \times 10^{-8}$M was administered. After reaching the plateau the preparations were washed for 30 minutes and a concentration 1 μM of the compound to be tested or of its vehicle was administered keeping it in contact for 30 minutes, after that a concentration of Big endothelin $3 \times 10^{-8}$M was administered again. The percentage of ECE-inhibition was expressed as $IC_{50}$ value (nM).

The values of NEP-inhibitory activity and ECE-inhibitory activity for some representative compounds of formula I are reported in the following table 1.

Table 1

NEP-inhibitory activity expressed as $IC_{50}$ value (nM) of the compounds 2, 4, 6, 9 and 13 in comparison to thiorphan, compound R-1 and compound R-2 and ECE-inhibitory activity expressed as $IC_{50}$ value (nM) of the above mentioned compounds in comparison to phosphoramidon.

| Compound | NEP-inhibitory activity $IC_{50}$ (nM) | ECE-inhibitory activity $IC_{50}$ (nM) |
|---|---|---|
| thiorphan | 8.3 | — |
| R-1 | 3.12 | — |
| R-2 | 8.8 | — |
| phosphoramidon | — | 50 |
| compound 2 | 1.5 | 2 |
| compound 4 | 2.1 | 2 |
| compound 6 | 12.6 | 1 |
| compound 9 | 2.7 | 4 |
| compound 13 | 5.0 | 3 |

The results reported in table 1 clearly show that the compounds of formula I, object of the present invention, are endowed with both NEP-inhibitory activity and ECE-inhibitory activity.

In particular, the NEP-inhibitory activity of the compounds of formula I is substantially comparable with that of the reference compounds and the ECE-inhibitory activity is significantly greater than that of phosphoramidon.

What we claim is:

1. A compound of the formula

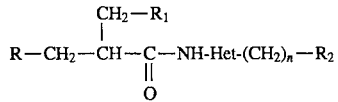

(I)

wherein

R is selected from the group consisting of a mercapto group and an $R_3COS$ group capable of converting to the mercapto group; $R_3$ is a $C_1$–$C_4$ alkyl group;

$R_1$ is selected from the group consisting of a hydrogen atom and a phenyl group optionally substituted by one or two groups selected among $C_1$–$C_4$ alkyl or alkoxy groups, hydroxy, halogen and trifluoromethyl groups;

$R_2$ is selected from the group consisting of a carboxy group, a $COOR_4$ and a

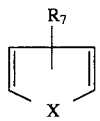

group capable of converting to the carboxy group; $R_4$ is a $C_1$–$C_4$ alkyl group or a phenylalkyl having from 1 to 4 carbon atoms in alkyl moiety;

$R_5$ and $R_6$, are the same or different, and are selected from the group consisting of hydrogen atoms, $C_1$–$C_4$ alkyl and $C_5$–$C_7$ cycloalkyl groups;

n is 0 or 1;

Het is a 5-membered heterocycle of the formula

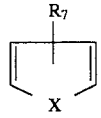

wherein X is selected from the group consisting of an oxygen atom and an NH group; $R_7$ is selected from the group consisting of a hydrogen atom, a $C_1$–$C_4$ alkyl group and a phenyl optionally substituted by $C_1$–$C_4$ alkoxy groups;

or a pharmaceutically acceptable salt thereof.

2. A compound according to claim 1 wherein R is a mercapto group or an $R_3COS$ group wherein $R_3$ is methyl; and $R_2$ is a carboxy group.

3. A compound according to claim 1 wherein R is a mercapto group or an $R_3COS$ group wherein $R_3$ is methyl; $R_2$ is a carboxy group; $R_1$ is phenyl optionally substituted by a $C_1$–$C_4$ alkyl or alkoxy group or by a halogen atom and Het is a heterocycle of the formula

wherein X is selected from the group consisting of an oxygen atom or an NH group and $R_7$ is a hydrogen atom.

4. A pharmaceutical composition for treating hypertension, renal failure and congestive heart failure containing a therapeutically effective amount of compounds of formula I in admixture with a pharmaceutically acceptable carrier.

* * * * *